(12) United States Patent
Alban et al.

(10) Patent No.: US 7,251,610 B2
(45) Date of Patent: Jul. 31, 2007

(54) CLINICAL DOCUMENTATION SYSTEM FOR USE BY MULTIPLE CAREGIVERS

(75) Inventors: Christopher Alban, Madison, WI (US); Khiang Seow, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 1180 days.

(21) Appl. No.: 09/950,185

(22) Filed: Sep. 10, 2001

(65) Prior Publication Data

US 2002/0062229 A1 May 23, 2002

Related U.S. Application Data

(60) Provisional application No. 60/233,950, filed on Sep. 20, 2000.

(51) Int. Cl.
*A61B 5/00* (2006.01)

(52) U.S. Cl. .......................................... 705/3; 704/270

(58) Field of Classification Search ................ 705/2–3; 704/270
See application file for complete search history.

(56) References Cited

U.S. PATENT DOCUMENTS

| | | | |
|---|---|---|---|
| 4,591,974 A | 5/1986 | Dornbush et al. |
| 4,667,292 A | 5/1987 | Mohlenbrock et al. |
| 4,839,806 A | 6/1989 | Goldfischer et al. |
| 4,893,270 A | 1/1990 | Beck et al. |
| 4,962,475 A | 10/1990 | Hernandez et al. |
| 5,072,383 A | 12/1991 | Brimm et al. |
| 5,072,412 A | 12/1991 | Henderson, Jr. et al. |
| 5,072,838 A | 12/1991 | Price, Jr. et al. |
| 5,077,666 A | 12/1991 | Brimm et al. |
| 5,088,981 A | 2/1992 | Howson et al. |
| 5,101,476 A | 3/1992 | Kukla |
| 5,253,362 A | 10/1993 | Nolan et al. |
| 5,301,105 A | 4/1994 | Cummings, Jr. |
| 5,319,543 A | 6/1994 | Wilhelm |
| 5,325,478 A | 6/1994 | Shelton et al. |
| 5,347,578 A | 9/1994 | Duxbury |
| 5,361,202 A | 11/1994 | Doue |
| 5,428,778 A | 6/1995 | Brookes |

(Continued)

FOREIGN PATENT DOCUMENTS

WO    WO-96/27163 A1    9/1996

(Continued)

OTHER PUBLICATIONS

Plaisant et al., "An Information Architecture to Support the Visualization of Personal Histories," Information Processing & Management, vol. 34, No. 5, 1998, pp. 581-597.

(Continued)

*Primary Examiner*—Andrew Joseph Rudy
*Assistant Examiner*—Vanel Frenel
(74) *Attorney, Agent, or Firm*—Boyle Fredrickson Newholm Stein & Gratz S.C.

(57) ABSTRACT

A computer-based system for recording, storing, and accessing clinical documentation in an acute care setting is provided. In an embodiment of the invention, a single electronic database or repository for storing clinical patient notes, provides multiple points of read/write access via a user interface operating on one or more client computers that are in real-time communication with the repository.

23 Claims, 16 Drawing Sheets

U.S. PATENT DOCUMENTS

| | | | |
|---|---|---|---|
| 5,450,593 A | 9/1995 | Howell et al. | |
| 5,471,382 A | 11/1995 | Tallman et al. | |
| 5,546,580 A | 8/1996 | Seliger et al. | |
| 5,557,515 A | 9/1996 | Abbruzzese et al. | |
| 5,574,828 A | 11/1996 | Hayward et al. | |
| 5,596,752 A | 1/1997 | Knudsen et al. | |
| 5,603,026 A | 2/1997 | Demers et al. | |
| 5,666,492 A | 9/1997 | Rhodes et al. | |
| 5,692,125 A | 11/1997 | Schloss et al. | |
| 5,724,584 A | 3/1998 | Peters et al. | |
| 5,740,800 A | 4/1998 | Hendrickson et al. | |
| 5,748,907 A | 5/1998 | Crane | |
| 5,751,958 A | 5/1998 | Zweben et al. | |
| 5,758,095 A | 5/1998 | Albaum et al. | |
| 5,760,704 A | 6/1998 | Barton et al. | |
| 5,772,585 A | 6/1998 | Lavin et al. | |
| 5,774,650 A | 6/1998 | Chapman et al. | |
| 5,778,346 A | 7/1998 | Frid-Nielsen et al. | |
| 5,781,442 A | 7/1998 | Engleson et al. | |
| 5,781,890 A | 7/1998 | Nematbakhsh et al. | |
| 5,802,253 A | 9/1998 | Gross et al. | |
| 5,823,948 A | 10/1998 | Ross, Jr. et al. | |
| 5,832,450 A | 11/1998 | Myers et al. | |
| 5,833,599 A | 11/1998 | Schrier et al. | |
| 5,838,313 A | 11/1998 | Hou et al. | |
| 5,842,976 A | 12/1998 | Williamson | |
| 5,845,253 A | 12/1998 | Rensimer et al. | |
| 5,848,393 A | 12/1998 | Goodridge et al. | |
| 5,848,395 A | 12/1998 | Edgar et al. | |
| 5,850,221 A | 12/1998 | Macrae et al. | |
| 5,867,688 A | 2/1999 | Simmon et al. | |
| 5,867,821 A | 2/1999 | Ballantyne et al. | |
| 5,899,998 A | 5/1999 | McGauley et al. | |
| 5,907,829 A | 5/1999 | Kida | |
| 5,915,240 A | 6/1999 | Karpf | |
| 5,924,074 A | 7/1999 | Evans | |
| 5,929,851 A | 7/1999 | Donnelly | |
| 5,946,659 A | 8/1999 | Lancelot et al. | |
| 5,960,406 A | 9/1999 | Rasansky et al. | |
| 5,974,389 A | 10/1999 | Clark et al. | |
| 5,983,210 A | 11/1999 | Imasaki et al. | |
| 5,987,498 A | 11/1999 | Athing et al. | |
| 5,997,446 A | 12/1999 | Brown | |
| 5,997,476 A | 12/1999 | Brown | |
| 5,999,916 A | 12/1999 | Peters et al. | |
| 6,014,631 A | 1/2000 | Teagarden et al. | |
| 6,016,477 A | 1/2000 | Ehnebuske et al. | |
| 6,021,404 A | 2/2000 | Moukheibir | |
| 6,029,138 A | 2/2000 | Khorasani et al. | |
| 6,037,940 A | 3/2000 | Schroeder et al. | |
| 6,047,259 A | 4/2000 | Campbell et al. | |
| 6,063,026 A | 5/2000 | Schauss et al. | |
| 6,067,523 A | 5/2000 | Bair et al. | |
| 6,081,786 A | 6/2000 | Barry et al. | |
| 6,082,776 A | 7/2000 | Feinberg | |
| 6,139,494 A | 10/2000 | Cairnes | |
| 6,154,726 A | 11/2000 | Rensimer et al. | |
| 6,182,047 B1 | 1/2001 | Dirbas | |
| 6,185,689 B1 | 2/2001 | Todd, Sr. et al. | |
| 6,188,988 B1 | 2/2001 | Barry et al. | |
| 6,263,330 B1 | 7/2001 | Bessette | |
| 6,272,593 B1 | 8/2001 | Dujari | |
| 6,275,150 B1 | 8/2001 | Mandler et al. | |
| 6,283,761 B1 | 9/2001 | Joao | |
| 6,289,368 B1 | 9/2001 | Dentler et al. | |
| 6,304,905 B1 | 10/2001 | Clark | |
| 6,317,719 B1 | 11/2001 | Schrier et al. | |
| 6,332,167 B1 | 12/2001 | Peters et al. | |
| 6,345,260 B1 | 2/2002 | Cummings, Jr. et al. | |
| 6,381,615 B2 | 4/2002 | Gaither et al. | |
| 6,389,454 B1 | 5/2002 | Ralston et al. | |
| 6,401,072 B1 | 6/2002 | Haudenschild et al. | |
| 6,415,275 B1 | 7/2002 | Zahn | |
| 6,678,698 B2 | 1/2004 | Fredell et al. | |
| 6,725,200 B1 | 4/2004 | Rost | |
| 6,757,898 B1 | 6/2004 | Ilsen et al. | |
| 6,856,989 B1 | 2/2005 | Zhou et al. | |
| 2001/0016056 A1 | 8/2001 | Westphal et al. | |
| 2001/0016853 A1 | 8/2001 | Kucala | |
| 2001/0041991 A1* | 11/2001 | Segal et al. | 705/3 |
| 2001/0049610 A1 | 12/2001 | Hazumi | 705/3 |
| 2001/0051888 A1 | 12/2001 | Mayhak, Jr. et al. | |
| 2001/0056433 A1 | 12/2001 | Adelson et al. | |
| 2002/0001375 A1 | 1/2002 | Alcott et al. | |
| 2002/0001387 A1 | 1/2002 | Dillon | |
| 2002/0002473 A1 | 1/2002 | Schrier et al. | |
| 2002/0002535 A1 | 1/2002 | Kitchen et al. | |
| 2002/0007287 A1 | 1/2002 | Straube et al. | |
| 2002/0022975 A1* | 2/2002 | Blasingame et al. | 705/3 |
| 2002/0046346 A1* | 4/2002 | Evans | 713/200 |
| 2002/0062229 A1 | 5/2002 | Alban et al. | |
| 2002/0188478 A1 | 12/2002 | Breeland et al. | |
| 2003/0061072 A1 | 3/2003 | Baker et al. | |
| 2003/0105648 A1* | 6/2003 | Schurenberg et al. | 705/2 |
| 2003/0110059 A1 | 6/2003 | Janas, III et al. | |
| 2003/0200726 A1 | 10/2003 | Rast | |
| 2004/0017475 A1* | 1/2004 | Akers et al. | 348/207.1 |
| 2005/0102146 A1* | 5/2005 | Lucas et al. | 704/270 |

FOREIGN PATENT DOCUMENTS

| | | |
|---|---|---|
| WO | PC-WO 98/13783 | 4/1998 |
| WO | WO-99/22330 A1 | 5/1999 |
| WO | WO-99/41682 A2 | 8/1999 |
| WO | WO-99/44162 | 9/1999 |
| WO | WO-99/44162 A1 | 9/1999 |
| WO | WO-99/63473 | 12/1999 |
| WO | PC-WO 00/29983 | 5/2000 |
| WO | WO-00/28460 | 5/2000 |
| WO | WO-00/65522 A2 | 11/2000 |
| WO | WO-02/29664 A1 | 4/2002 |

OTHER PUBLICATIONS

Fabbretti et al., "Applying the Object Paradigm to a Centralized Database for a Cardiology Division," International Journal of Bio-Medical Computing, vol. 42, 1996, pp. 129-134.

Van De Velde, "Framework for a Clinical Information System," International Journal of Medical Informatics, vol. 57, 2000, pp. 57-72.

Egan et al., "Computers and Networks in Medical and Healthcare Systems," Comput. Biol. Med., vol. 23, No. 3, 1995, pp. 355-365.

Michihiro Hazumi and Toshio Kawamoto, "Development of Electronic Medical Record System," NEC Res. & Develop., vol. 41, pp. 102-105, Jan. 2000.

"HCS Order Communications Module," web.archive.org/hcsinteractant.com, 2000, pp. 1-3.

Ebidia et al., "Getting Data Out of the Electronic Patient Record: Critical Steps in Building a Data Warehouse for Decision Support," SIMS University Health Network, Dept. of Medicine, University of Toronto, Canada, Nov. 8, 1999, pp. 1-5.

"Patient1 Vista", PerSe Technologies, www.per-se.com/web.archive.org, 2000, 2 pages.

"Sunrise Clinical Manager", Eclipsys, Sunrise Clinical Overview, www.eclipsnet.com/web.archive.org, 1999, 1 page.

"American Medical Management Selects Tandem Computers as Systems Partner", PR Newswire, Feb. 20, 1997, 2 pages.

"Premier Members Select Cerner's Clinical Data Repository as a Result of Exclusive Endorsement", PR Newswire, Feb. 19, 1997, 2 pages.

"Physicians and Staff Go Online with Cerner's Clinical Data Repository and Orders Management", PR Newswire, Mar. 4, 1996, 2 pages.

"Patient1", PerSe Technologies, www.per-se.com/web.archive.org, 2000, 4 pages.

"Sunrise Clinical Manager," Advanced Clinical Solutions, ECLIPSYS, www.eclipsys.com, Dec. 2002, 4 pages.

"News & events," ECLIPSYS, www.eclipsys.com, Apr. 16, 2002, 3 pages.

"Horizon Clinicals," McKesson Corporation, www.mckesson.com, 2003, 2 pages.

"Acute Care EMR—Solutions," Cerner Corporation, www.cerner.com, 2002-2003, 2 pages.

"Foundation," IDX Systems Corporation, www.idx.com, 1999-2004, 2 pages.

"Supporting the Work of Clinicians," IDX Systems Corporation, www.idx.com, 1999-2004, 1 page.

"Autonomy Update™", Product Brief, Autonomy Inc., www.autonomy.com, Mar. 2003, 2 pages.

"Brio.Portal", Sun Solutions Catalog, Sun Microsystems, www.sun.com, 1994-2002, 1 page.

"Portal-in-a-Box™," Product Brief, Autonomy Inc., www.automony.com, Apr. 2002, 6 pages.

"Actuate Software," Sun Solutions Catalog, Actuate Corporation & Sun Microsystems, www.sun.com, 2002, 24 pages.

"CDR-Web," Reliance Software Systems, Website, 2000, 1 page.

Marietti, "O' Pioneers!," Healthcare Informatics, Website, May 1999, 9 pages.

Johnson, "Today's CDRs: The Elusive Complete Solution," Healthcare Informatics, (Website), Jul. 1997, 7 pages.

Andrew et al., "Computer-Based Patient Records—Venturing Off the Beaten Path: It's Time to Blaze New CPR Trails," Healthcare Informatics, (Website), May 1997, 17 pages.

"EMR Features," Care is #1, 1999-2000, 1 page.

"Enterprise Systems Management," Cerner Corporation, www.cerner.com, Sep. 13, 2001, 5 pages.

"HealthMatics™ Office", Healthmatics Office, Website, 3 pages, (date unknown).

Clinicomp, Intl., Website, 1999-2000, 1 page.

"ExcelCare Windows", Website, 2 pages (date unknown).

"IC-Chart Information", Integreat, Website, 1 page, (date unknown).

"Managing mail messages with rules," Microsoft Outlook Help Manual, Website, Version 6, 5 pages Jun. 24, 2002.

Mercando, "Appointment Scheduling on Computer", PACE, vol. 20, Jul. 1997, pp. 1860-1862.

EncounterPRO, the Workflow Enabled CPR/EMR from JMJ Technologies, JMJ Technologies, Inc., www.jmjtech.com, Nov. 8, 2002, 6 pages.

"Expeditor Systems—The Patient Flow Systems Experts", Expeditor Systems, www.expeditor.com, 2001, 3 pages.

"Working with Patient Lists," EpicCare Inpatient Electronic Medical Record Jul. 2000 User's Guide, Epic Systems Corp., Section 10.5-10.6, 3 pages.

"Patient Lists," EpicCare Inpatient Electronic Medical Record Jul. 2000 User's Guide, EPIC Systems Corp., Section 11.3-11.4, 3 pages.

"Oacis—Census Management," DINMAR (U.S.) Inc., www.oacis.com, 2002, 2 pages.

"Clinician Documentation with EMR," Clinicomp, Intl., www.clinicomp.com, 1999-2002, 1 page.

"Essentris™ CPOE", Clinicomp, Intl., www.clinicomp.com, 1999-2002, 2 pages.

"Essentris™ GDR," Clinicomp, Intl., www.clinicomp.com, 1999-2002, 2 pages.

"Intensivist Tools," Clinicomp, Intl., www.clinicomp.com, 1999-2002, 2 pages.

"CMRxp—Computerized Medical Records Powered by Experience!!," Electronic Medical, Records (EMR)xp Experience, Chartcare, Inc., www.chartcare.com, Mar. 5, 2003, 2 pages.

"Dr-InBasket-Lab Results, Messaging and To-Do's," Chartcare, Inc., www.chartcare.com, Mar. 5, 2003, 3 pages.

"PatInfo-Patient Information Handouts," PatInfo-Pateint Demographics Software, Chartcare, Inc., www.chartcare.com, Mar. 5, 2003, 2 pages.

"Recall-Patient Health Maintenance," Chartcare, Inc., www.chartcare.com, Mar. 5, 2003, 3 pages.

"LabTrack-Lab Ordering & Results Tracking," LabTrack-Lab Result Tracking Software, Chartcare, Inc., www.chartcare.com, Mar. 5, 2003, 3 pages.

"Rx-MedTrack-Prescription Writing/Medication Tracking," Rx-MedTrack-Prescription Writing Software, Chartcare, Inc., www.chartcare.com, Mar. 5, 2003, 2 pages.

"The Right Tools," Product Description, Integreat Inc., www.igreat.com, 2003, 1 page.

"IC-Chart Additional Modules," Integreat Inc., www.igreat.com, 2003, 2 pages.

"Services," Integreat Inc., www.igreat.com, 2003, 2 pages.

Grimson et al., *Interoperability Issues in Sharing Electronic Healthcare Records-the Synapses Approach*, IEEE, 1997, pp. 180-185.

McDonald et al., *The Regenstrief Medical Record System: a quarter century experience*, International Journal of Medical Informatics, vol. 54, 1999, pp. 225-253.

International Search Report PCT/US01/29125 dated Mar. 14, 2003.

* cited by examiner

Athens, Jill - New Note by SEEGER, MARTY

Cosign Required

Note Type: Progress Notes

S: feeling well this AM. Wants to go home. Continued to feel he is improving. Thinks he has more strength in arm and eating went okay yesterday. Slept ok.
O: BP 132/80, HR 76, RR 16
HEENT: pupils equal and reactive, gag intact
Neck: supple, carotids2+, no bruits
Lungs: clear, decreased in bases
Heart: regular rhythm, normal rate
Abd: soft, nontender
Neuro: L facial droop mild at this point
Motor: RUE 5/5, RLE 5/5, LUE 4/5, RLE 5/5
Sensory: intact to light touch
Reflexes:
    R - biceps 2+, triceps 2+, patellar 2+, achilles 2+
    L - biceps 2+, triceps 2+, patellar 2+, achilles 2+

Labs

Copy Prev.  Voice On  Pend  Accept  Cancel

FIG. 4

Athens, Jill - New Note by SEEGER, MARTY

Note Type [ Progress Notes ]  — 60

Juarez, Mark F    Medicine Resident    04/10/2001 08:42 AM

S: feeling well this AM.  Wants to go home.  Continued to feel he is improving.  Thinks he has more strength in arm and eating went okay yesterday.  Slept ok.

O: BP 132/80, HR 76, RR 16
HEENT: pupils equal and reactive, gag intact
Neck: supple, carotids2+, no bruits
Lungs: clear, decreased in bases
Heart: regular rhythm, normal rate

— 66
— 68

Resident note reviewed.
Agree with findings and assessment.
Plan includes increased mobilization, PT as needed, repeat CT scan in AM, and transfer to the floor
Expect D/C in a day or two

— 70

— 64

[ Copy Prev. ]  [ Voice On ]  [ Pend ]  [ Accept ]  [ Cancel ]

CLINICAL DOCUMENTATION SYSTEM FOR USE BY MULTIPLE CAREGIVERS

CROSS-REFERENCE TO RELATED APPLICATIONS

This application claims priority to U.S. Provisional Application Ser. No. 60/233,950, filed Sep. 20, 2000, the disclosure of which is hereby expressly incorporated herein by reference.

FIELD OF THE INVENTION

The invention relates generally to information management systems for use within the healthcare enterprise, and more particularly, to a system for documenting clinical patient information generated by multiple caregivers.

BACKGROUND OF THE INVENTION

During the course of a patient's stay in an inpatient or acute care facility, the patient will be seen by a variety of health care providers as they review the patient's status, recommend treatments and protocols, provide care, order tests, etc. Providers must record all of their activities and decisions for the patient, and efficient communication of this information between all of a patient's caregivers is key to the problem of providing a patient with the best possible care.

Existing approaches to this problem typically center on some kind of shared patient record. A shared paper chart kept in or near the patient's room represents perhaps the most common but also the least effective approach. A shared paper chart offers very limited security and virtually no simultaneous access for either viewing or editing the patient's hospital record. What's more, as information is eventually added to the patient's record from a large number of caregivers, it becomes increasingly difficult and time consuming to identify and review appropriate information for a particular situation.

A computer-based approach can solve some of these problems by providing a central repository for storing and accessing clinical documentation for a patient, and in recent years many computer-based clinical documentation systems have been conceived and implemented for both ambulatory and acute care settings. However, these systems typically demonstrate weaknesses and problems that result in a failure to ensure efficient communication between a patient's acute caregivers. Problems with these systems include a failure to address one or more of the following needs:

providing a single point of access to the information recorded by all of the patient's caregivers during an acute care episode;

providing simultaneous access to a patient's chart for both viewing and editing from different locations while maintaining data integrity;

providing role-based security to limit each caregiver's viewing and editing access to a patient's chart;

providing user-linked time-stamps for both data entry and review that a) make it easy to present a longitudinal view of the patient record, b) provide a means for a user to quickly see information that's been added to the patient's record since the user's last review, and c) providing for note cosign by one or more caregivers;

providing for storing and sorting patient notes according to caregiver's roles, service areas and etc.;

providing easy to use filter and search tools that allow a caregiver to quickly identify and review clinically appropriate information for a given situation;

providing for entering data other than entirely manual keyboard entry, for example automated text-entry options, dictation, voice recognition, etc.;

providing for incorporating available information relevant to a patient's acute care episode, for example emergency room (ER) notes, hospital discharge summaries etc.

Thus, there is a need for a clinical documentation system that addresses these needs within the healthcare enterprise.

BRIEF DESCRIPTION OF THE DRAWINGS

FIG. 4 is a graphic representation of a new/edit window function in accordance with an embodiment of the invention.

FIG. 5 is a graphic representation of a cosign function in accordance with an embodiment of the invention.

DETAILED DESCRIPTION OF THE PREFERRED EMBODIMENTS

Figure 1:
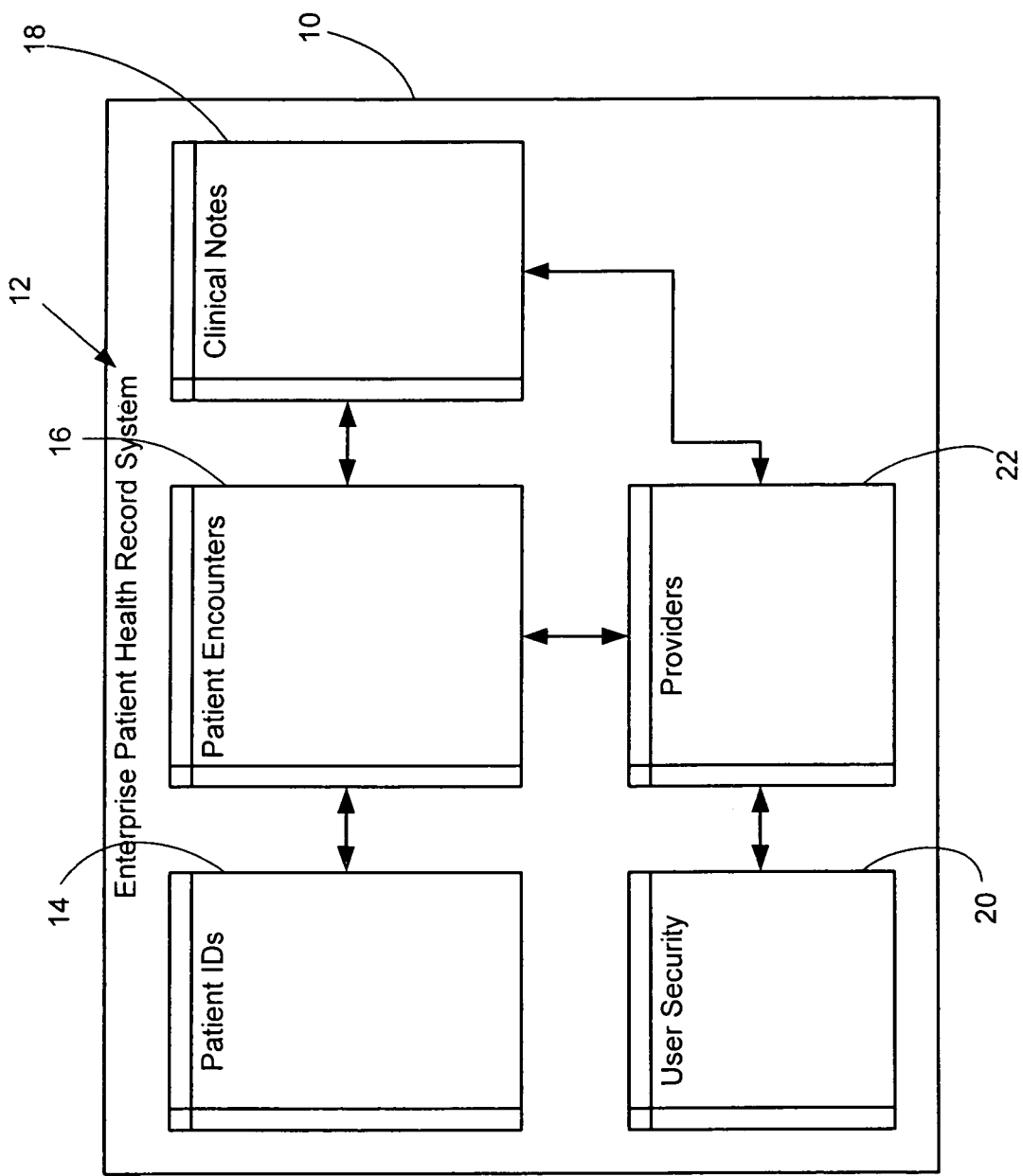
FIG. 1 is a block diagram illustrating a patient health record system in accordance with an embodiment of the invention.

A computer-based system for recording, storing, and accessing clinical documentation in an acute care setting is provided. In an embodiment of the invention, a single electronic database or repository for storing clinical patient notes is accessed via a plurality of client workstations coupled, e.g., networked, to the single electronic database providing multiple points of read/write access via a user interface operating on one or more client computers that are in real-time communication with the repository.

The system may provide for storing and sorting patient notes according to caregiver's roles, service areas, etc., and may include a data access scheme that provides simultaneous view access to a patient's chart for both viewing and editing, and which automatically locks an individual note from write access when it is being edited by someone else. In addition, an embodiment of the invention may include a role-based user-security scheme that can be configured to limit each caregiver's viewing and editing access to a patient's chart to only appropriate types of information. An embodiment of the invention may also include a user-linked time-stamping mechanism for both data review and entry and a corresponding user interface that a) presents a longitudinal view of the patient record and b) permits a user to easily filter for information that's been added to the patient's record since the user's last review. Longitudinal view refers to an ability to display and view notes from a patient's previous contacts over time providing essentially a holistic view of the patient's contact history.

An additional embodiment of the invention may provide for importing (either manually or automatically) available information relevant to a patient's acute care episode from external sources where necessary, for example ER notes, hospital discharge summaries, etc., and for viewing, filtering, and searching this information along with the other patient notes. Still further, an embodiment of the invention may provide for importing, storing and viewing graphic and other multi-media information and linking it to the appropriate entries in a patient's acute care record.

A system according to the embodiments of the invention may include a user interface coupled to the enterprise health record system to provide single point of access for information recorded by all of a patient's caregivers during an acute care episode. The user interface may include predefined role-based filters and/or an easy to use custom filter and search options that allow a caregiver to quickly identify and review clinically appropriate information for a given situation. The user interface allows caregivers to choose between a number of data entry options, including manual keyboard entry, automated text-entry, dictation, voice recognition, etc. The user interface may also allow caregivers to file a note (to store it on the server) and mark it either as complete or pending, and may further allow a caregiver to edit a note while also reviewing other information in the patient's acute care record. In accordance with the embodiments of the invention, the user interface makes it easy for users to take appropriate follow up actions for specific entries in a patient's acute care record, for example, for a supervising physician to review, document, and cosign an entry made by a resident.

Figure 2:
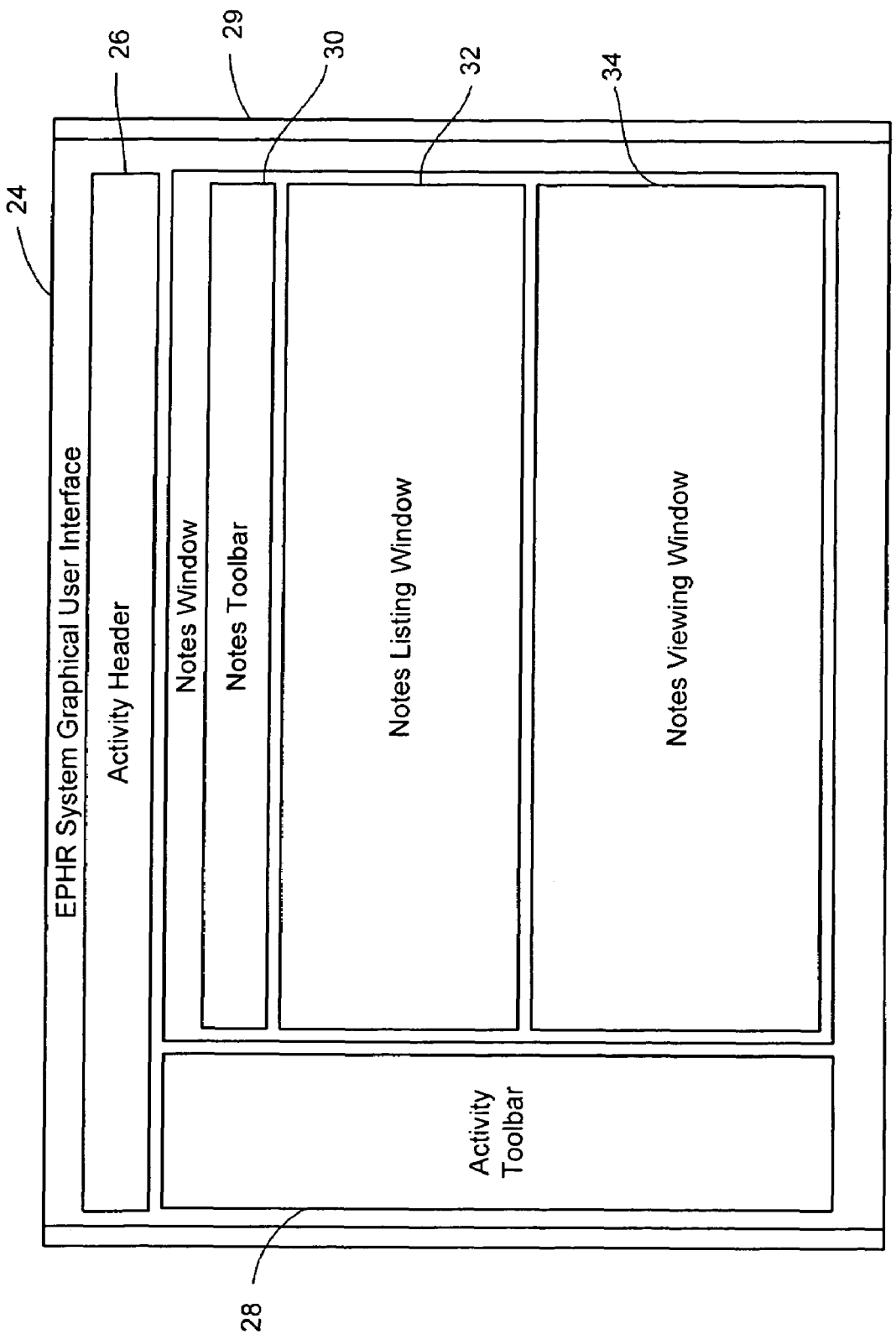
FIG. 2 is a block diagram illustrating a graphic user interface of the patient health record system illustrated in FIG. 1.

Referring to FIG. 1, an enterprise patient health record system 10 includes a number of data elements 12 for supporting the information needs of the healthcare enterprise. As shown in FIG. 1, the system 10 includes a patient ID element 14, a patient encounter element 16, a clinical notes element 18, a user security element 20 and a providers element 22. These elements, for example, provide to the system 10 respective data services. For example, the patient ID 14 includes a data structure for organizing and storing patient identification information and may incorporate processing and communication capability to allow the element to interface with the other elements of system 10 for receiving, organizing and storing patient information and for retrieving and delivering patient information. Of course the processing and communication capability may be centralized within the system 10, in which case the respective element would include just the appropriate data structure for organizing and retaining data. The system 10 drives a graphic user interface (GUI) 24 shown in FIG. 2. The GUI 24 may be supported on any number of client workstations coupled, e.g., networked, to the system 10. As such, a user may log into the system 10 at any of the workstations from virtually any location, including remotely from the healthcare facility via a private network or a public network, e.g., the Internet.

The GUI 24 may have a web browser or other suitable appearance, and includes an activity header 26, an activity toolbar 28, a notes toolbar 30, a notes listing window 32 and a notes viewing window 34. The activity header 26 may provide current patient information, such as patient name, sex, age, insurance and other patient demographic information. The activity toolbar 28 contains point-and-click activity selections, which allow the user to activate various activities within the system 10, including the patient's notes activity.

Figure 3:
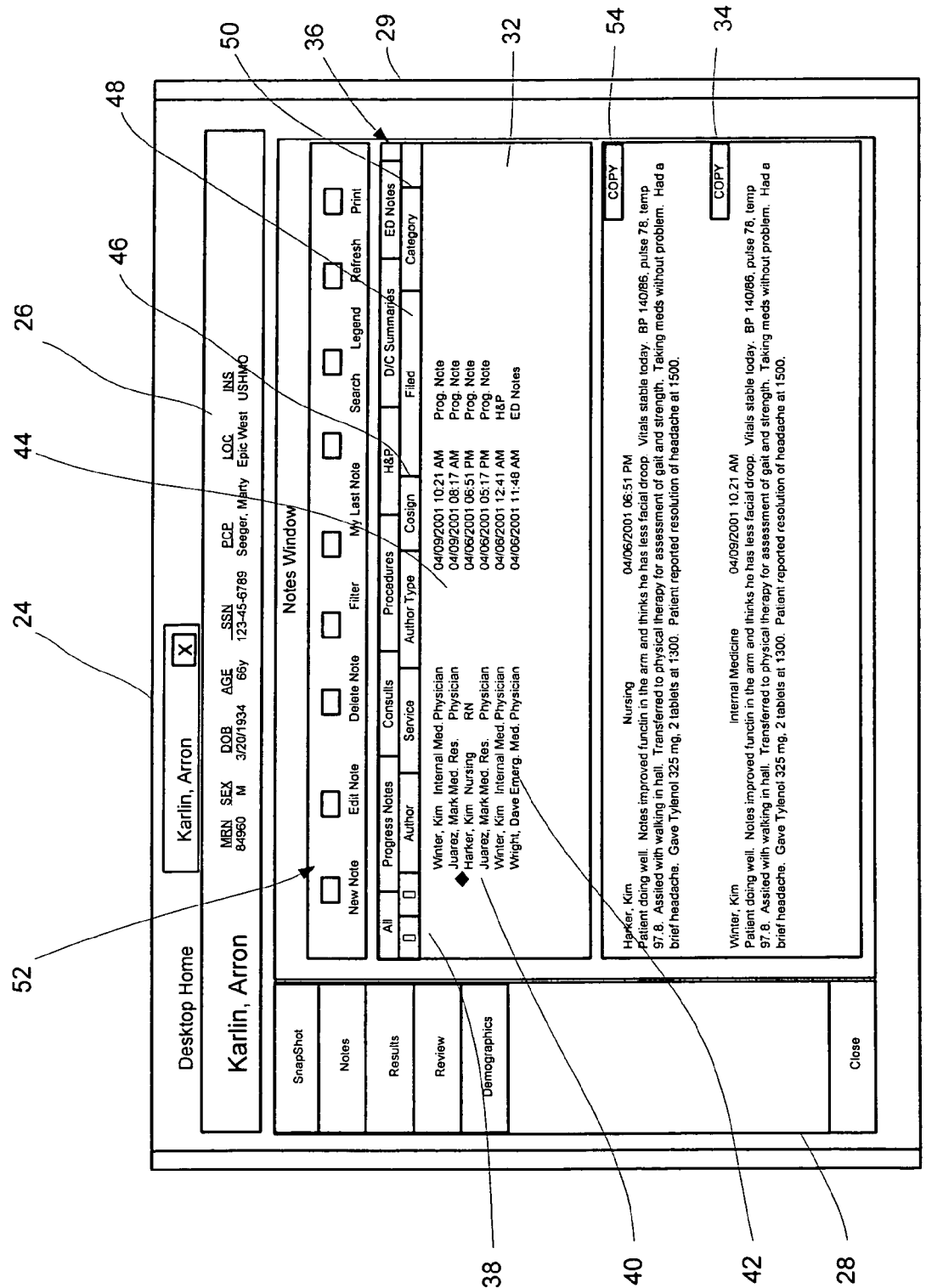
FIG. 3 is a graphic representation of the graphic user interface illustrated in FIG. 2.

Referring generally to FIG. 3, the notes listing window 32 provides the user with a listing of all or selectively filtered notes for the current patient. Selecting a note from the listing window 32 causes the note to be displayed in the notes viewing window 34. Notes within the listing window 32 may be color coded and/or may include a graphic representation, e.g., an icon, to depict the author, author type, medical service, etc., associated with the note. The author, author type, medical service, note time and date, etc., may be depicted with the body of the note in the viewing window 34. Additionally, scrolling may be provided to facilitate viewing of the notes within the viewing window 34.

With more particular reference to FIG. 3, the notes listing window 32 may include a plurality of note tabs 36 indicating various categories of notes. The user may click on one of the tabs to display a list of notes for that category. Only the notes written by authors that match a current filter criteria, described more fully below, are displayed. The notes listing window also includes an author symbol column 38. Within the author symbol column 38, a graphic representation, i.e., an icon or symbol, may be displayed indicating the author type. The notes listing window also includes an author segment 40 to display the name of the provider who wrote the note, the service segment 42 to display the name of the medical service to which that user belongs and an author type segment 44 indicating the role of the provider writing the note. The specific authors types listed may be configured by a system administrator and/or by the user. A cosign segment 46 displays the word "required" for notes requiring a cosign. When a cosign is required, a cosign button (not depicted) appears adjacent the note in the listing window 32. The cosign button opens a cosign window (FIG. 5) to allow the cosigning user(s) to enter the required cosign(s). A filed segment 48 displays the date and time the note was accepted., and a category segment 50 indicates the category of the note when all notes are being displayed. In addition, a copy button 54 appears adjacent each note in the viewing window 34. The copy button 54 causes a copy of the text of the note to be copied to a clipboard, e.g., the Windows clipboard, allowing the text to be pasted into a new note and/or into a different application.

Within the notes toolbar 30 there are a number of buttons 52 corresponding to functions related to the patient's notes activity allowing the user to select a particular function using a point-and-click or similar action. New note and edit note functions each opens a new/edit note window 56 shown in FIG. 4 and allows the user to enter the new note or edit the pending note. The edit notes function may only be used with the user's own notes, and the user is not permitted to edit another user's notes. Moreover, once a note is accepted, it generally may not be edited or deleted. The window 56 includes a number of fields including a cosign required box 58, which allows the user to indicate whether a cosign for the note will be required. A note type selection 60 is provided to allow the user to enter the category of the note, such as: progress notes, consult notes, procedures, History and Physical notes, Discharge summaries and Emergency Department notes.

Another note type that may be provided is referred to as a "tagged" note. A tagged note may generally be any note type supported by the system 10, but the tagged note includes tag data. The tag data sub-classifies or sub-types the note. One feature of the tag data is that it allows the notes to be efficiently segregated and collected for report generation. For example, certain notes may relate only to casual or general comments that would not ordinarily by reported. These notes might be tagged "casual comments." Other notes may relate to the patient's treatment plan that would be reported. These notes might be tagged "treatment plan." A filter search by author would retrieve both the casual comments and the treatment plan notes, while a search by author and the "treatment plan" tag would provide only those notes by that author that are also tagged "treatment plan."

The user enters the note text in a note text box 62. Note text may be entered using many common wordprocessing functions including typing, copying, cutting and pasting, by using drafting assist tools, such as the SmartSet documentation tool available from Epic Systems Corporation of Madison, Wis., or by dictation, which may include voice recognition. The user selects the entry method using the appropriate one of the buttons 59. Using dictation alone causes the note to be recorded for later transcription to text, while using dictation in conjunction with voice recognition may provide an instantaneous text transcription. A note editing toolbar 64 provides text editing and formatting functions to assist the user in entering the note text.

When a cosign is required, the cosigning user opens a cosign note window 66 shown in FIG. 5 using the cosign button 52 (FIG. 3). The type of cosign required is specified by cosign data specified for the note by the author. The required cosign may specify a single caregiver, for example, the author's attending physician. Alternatively, the required cosign may specify cosigns from multiple caregivers from one or more medical services. The cosign window 66 allows the cosigning user(s) to indicate that the user's note has been reviewed and approved by the cosigner. The user's note is displayed in a note text window 68, and the cosigning user(s) enters their approval/disapproval and any appropriate comments in a cosign text box 70. Once the cosigning user(s) accepts the cosign note, the original note and the cosign note are linked so other users may easily see relevant information from both.

A delete note function allows the user to delete the pending note. The user may not delete another user's notes nor may the user delete a note once it has been accepted; however, it may be possible to soft delete a note. There may be an occasion that a note should be deleted, for example, if the note is out of date or in error. In some instances, governmental regulations may prohibit deleting of information from the patient's record. Soft deleting allows the user to indicate the deleted status of the note while not permanently removing the note from the system.

Figure 6:
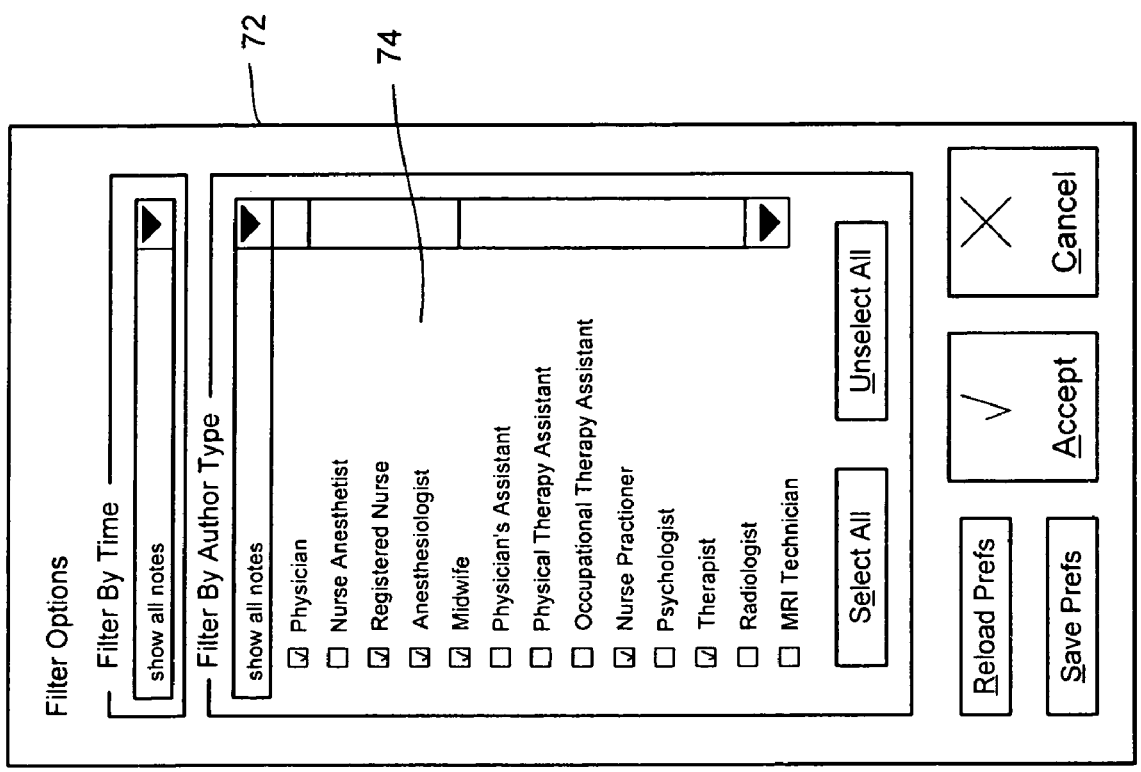
FIG. 6 is a graphic representation of a filter function in accordance with a preferred embodiment of the invention.

A filter function allows the user to modify the types of notes that appear in the notes listing window and opens a filter options window 72 shown in FIG. 6. There are many possible filter criteria that may be implemented. For example, notes may be filtered by time, author type, author, medical service, etc. For example, selecting to filter by author type causes a listing of the various author types 74 to appear in the filter options window 72. The user selects a particular author type, such as physician, registered nurse, etc., and after the user accepts the criteria, the notes for that author type are displayed in the listing window 32.

A "my last note" function causes the user's most recent note in the category to be highlighted. A search function opens a find window (not depicted), in which the user may enter specific words or phrases as criteria to search within the existing notes. The search may be limited to a category of notes, or may encompass multiple categories or all notes.

A legend/notes function toggles the notes listing window 32 between a notes state and legend state. In the notes state, displayed within the listing window 32 is a listing of the filtered notes for the current patient in reverse chronology order. In the legend state, displayed within the listing window 32 is a key explaining the symbols and colors associated with the notes. As described above, to distinguish notes, by type, author or otherwise, the notes may be displayed in corresponding colors and/or may include a graphic representation, e.g., an icon, adjacent the note to designate, for example, its author type, and the legend state permits viewing of this representative information.

A refresh function updates the information displayed in the notes listing window 32. If other users have written notes for the current patient since the last refresh, these new notes will now appear in the listing window 32. If a filter option has been selected, the listing is refreshed using the current filter criteria. In addition, the information displayed in the notes listing window 32 may periodically be updated at a rate specified by a system administrator and/or by the user.

A print function causes the selected note to be printed. As an option, the user may select to print all of the notes by selecting an all notes function associated with the print button.

Figure 7:
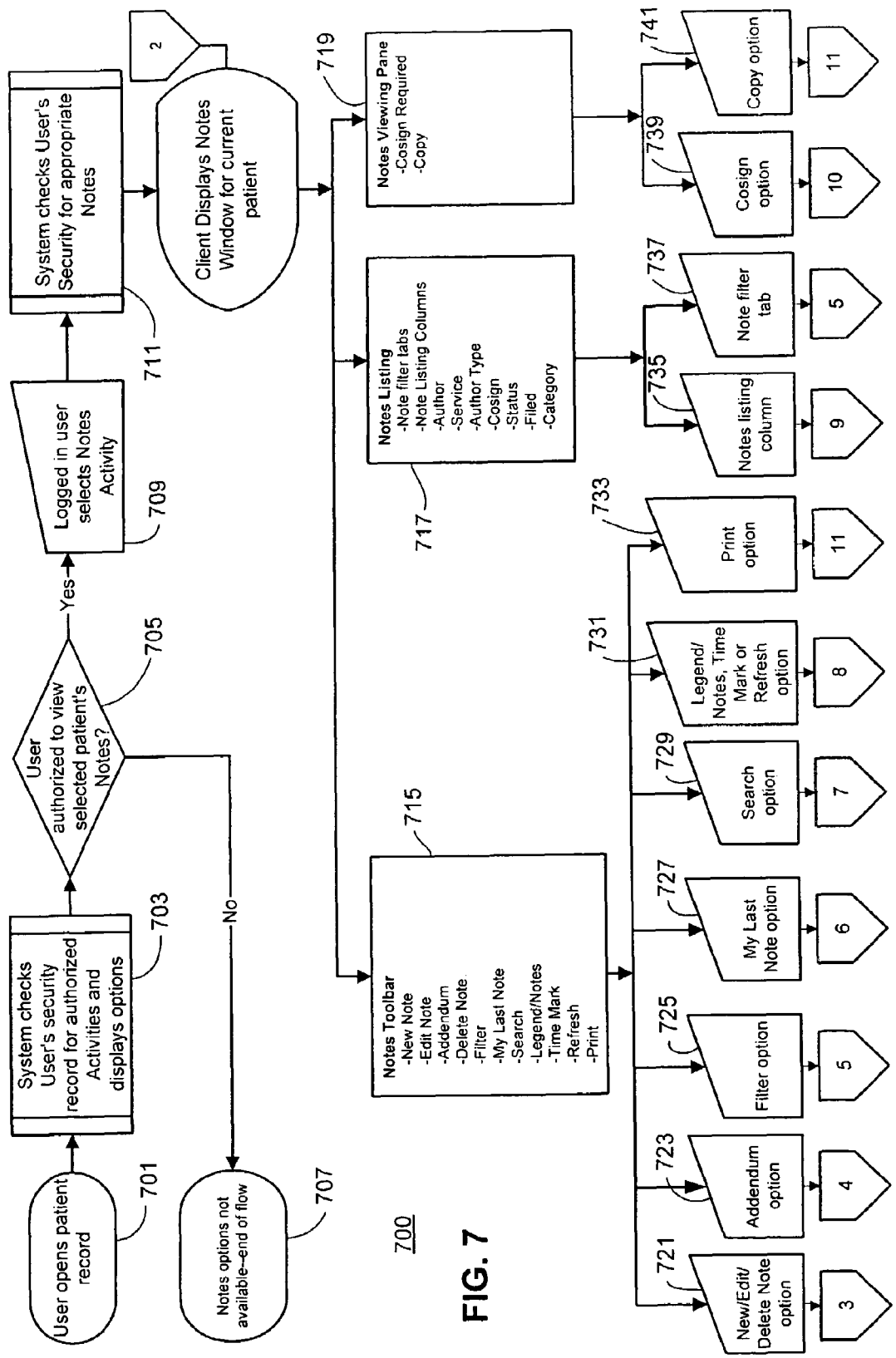
FIG. 7 is a flowchart representing the general workflow associated with a system in accordance with an embodiment of the invention.

Referring now to FIGS. 7-15, and initially to FIG. 7, workflows associated with the operation of the system 10 are described in greater detail. Workflow 700 begins with a logged in user opening an available patient record, 701. The system 10 checks the user's security record for authorized activities, and displays the authorized activities in the activity bar 28, 703. If the user is not authorized to view patient notes, 705, then the notes option is not made available to the user via the activity bar 28, 707. Otherwise, the user selects the patient's notes activity from the activity bar 28, 709, and the system checks the user's security to determine the notes the user may access, 711, and these notes are displayed in the listing window 32, 713. The user may then add, edit, filter, search, cosign, etc. notes by selecting such functions from the appropriate one of the notes toolbar, 715, the notes listing window, 717 or the notes display window, 719. Links, 721-741, take the user to a workflow corresponding to the selected activity.

Figure 8:
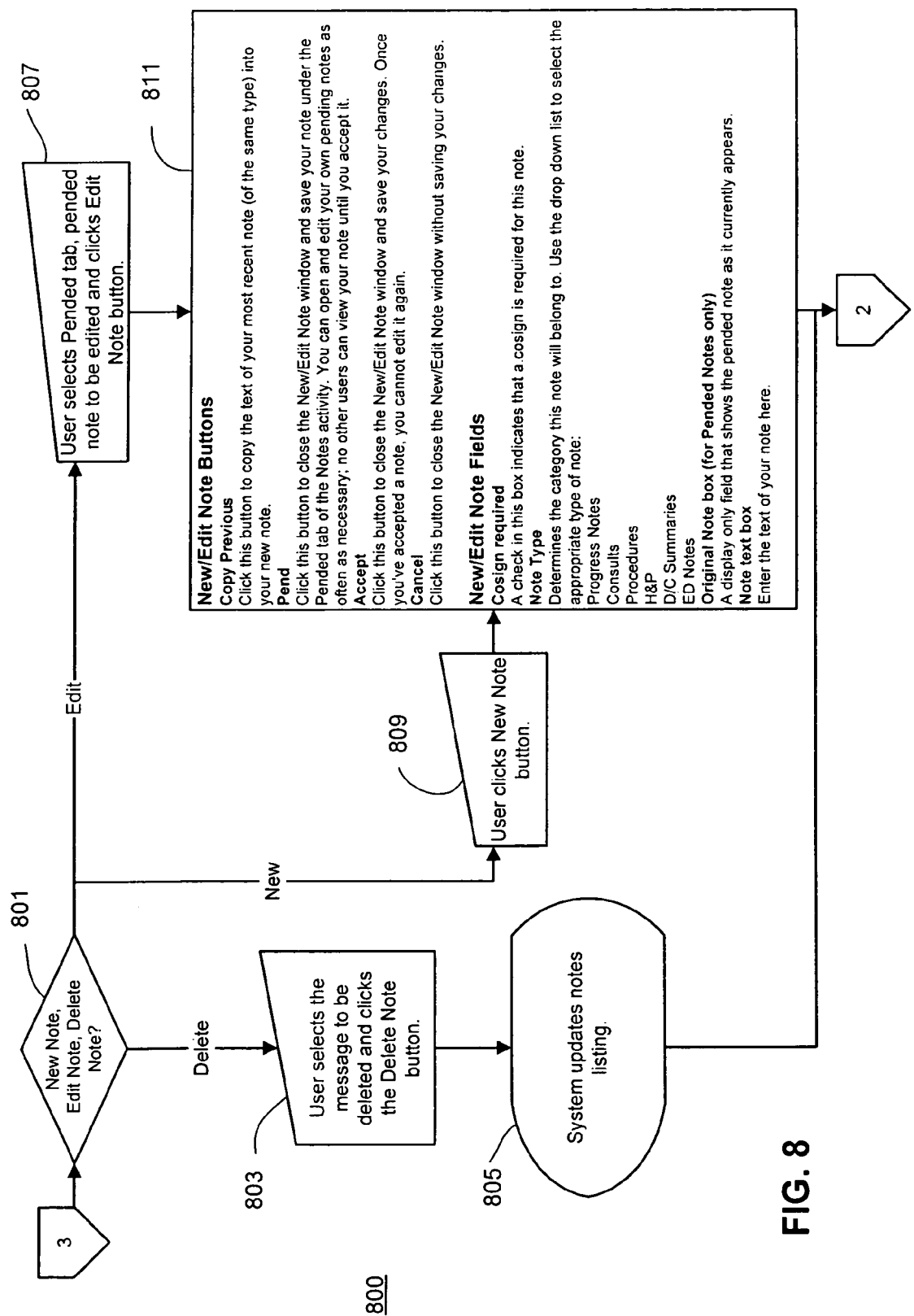
FIG. 8 is a flowchart representing a workflow for adding, editing or deleting a patient note in accordance with an embodiment of the invention.

From link 721 for the new/edit/delete functions, the workflow 700 proceeds to the workflow 800 illustrated in FIG. 8. If the user wants to delete a note, 801, the user selects the note to be deleted and clicks a Delete button, 803. The system 10 updates the notes listing, removing the deleted note from all tabs on which it was displayed, 805. If the user wants to edit a note, 807, the users selects an Edit Note button opening the new/edit note window 56, 811. Similarly, if the user wants to create a note, 809, the user selects a New Note button opening the new/edit note window 56, 811. The user has several options for creating/editing a patient note, as described above. Once the note is created/edited, the user clicks a Pend button to close the new/edit note window 56 and save the note under a pending notes tab. Notes that have not been accepted may be saved under the pending notes tab of the new/edit notes window 56. Other users may not view pending notes and the user may edit or delete the note until it has been accepted. If the user wants to accept the note, the user clicks an Accept button to close the new/edit notes window 56 and save the note. Once the note is accepted, it cannot be edited and may only be soft deleted. There is also a Cancel button allowing the user to cancel out of the new/edit notes window without saving changes.

Figure 9:
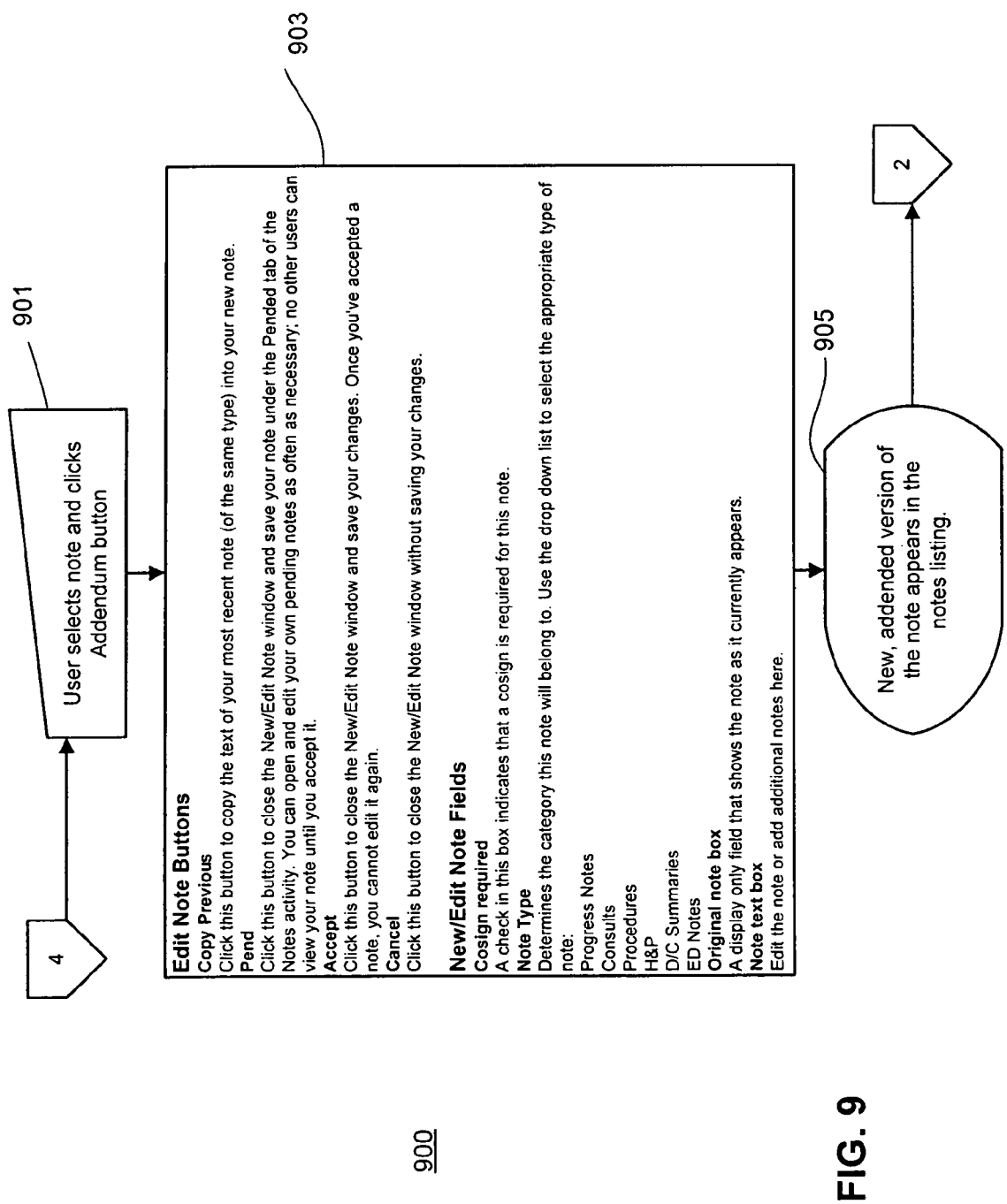
FIG. 9 is a flowchart representing a workflow for addending a patient note in accordance with an embodiment of the invention.

From the link 723 for the note addendum function, the workflow 700 proceeds to the workflow 900 illustrated in FIG. 9. If the user wants to create an addendum to a note, the user selects the note and selects the addendum function opening the new/edit note window 56, 901. Because a note cannot be edited and only may be soft deleted once accepted, adding an addendum provides for adding or updating note information. Editing of the addendum is the same as that for editing or creating a note, except that the original text of the note may not be edited, 903. When completed, the user accepts the addendum, and the new addended version of the note appears in the notes listing window 32 with a date and time stamp link to the original note, 905.

Figure 10:
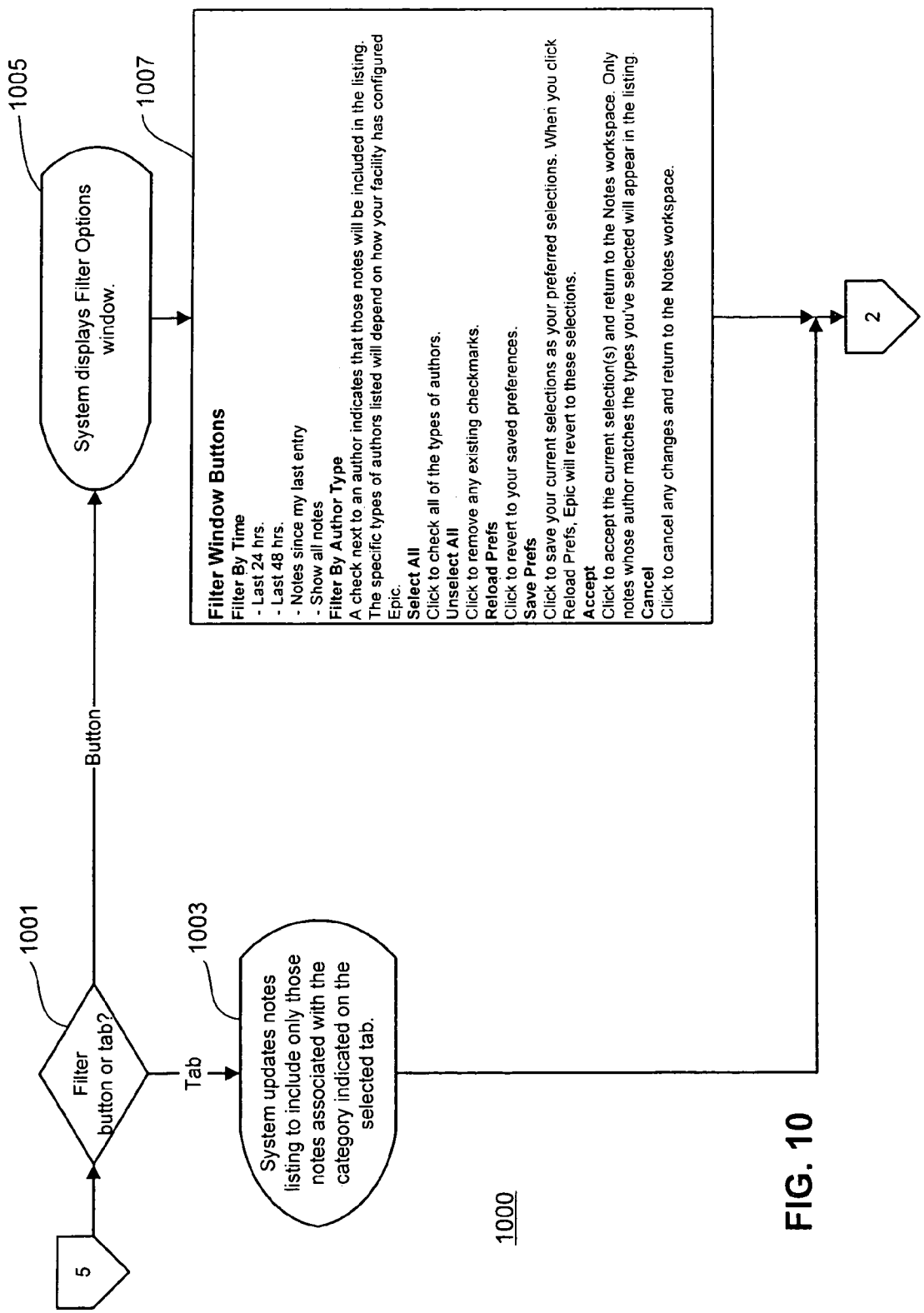
FIG. 10 is a flowchart representing a workflow for filtering patient notes in accordance with an embodiment of the invention.

From the link 725 for the note filter function or the link 737 for the note filter tab, the workflow 700 proceeds to the workflow 1000 illustrated in FIG. 10. If the user selects the filter tab, 1001, from the notes listing window 32, the system 10 updates the notes listing to include only those notes associated with the category indicated on the selected tab in reverse chronological order, 1003. If the user selects the filter button, 1001, the filter window 72 is opened, 1005, allowing the user to set filter criteria, 1007. Filter criteria includes, but is not limited to, filter by time, filter by author type, all notes, unselect all, reload filter preferences, save filter preferences, accept or cancel. Filter by time options include filtering by time periods such as the previous 24 or 48 hours, since last note entry or all notes. The select all allows the user to select all author types, and the unselect all allows the user to unselect all author types. The user may create preferred filter configurations, and these preferences may be saved in connection with the user profile. This permits the user to easily filter and view the notes most commonly associated with their work activity. Accepting the filter selections returns the user to the notes window 29.

Figure 11:
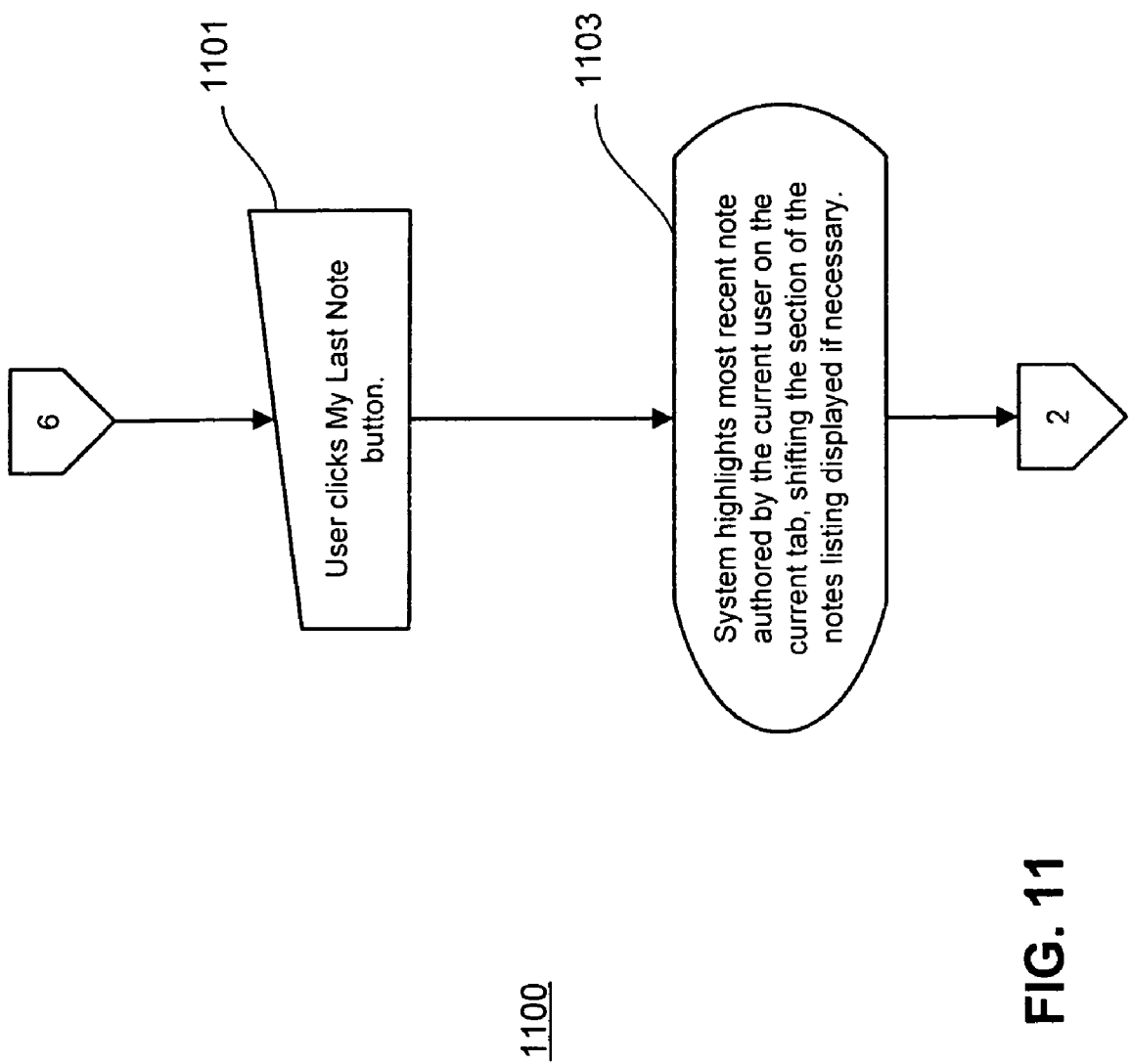
FIG. 11 is a flowchart representing a workflow for retrieving and displaying a last entered patient note in accordance with an embodiment of the invention.

From the link 727 for the "my last note" function, the workflow 700 proceeds to the workflow 1100 illustrated in FIG. 11. If the user selects the "my last note" button, 1101, the system 10 automatically highlights the most recent note authored by the user, 1103. The notes listing is scrolled as necessary to permit display of the user's last note.

Figure 12:
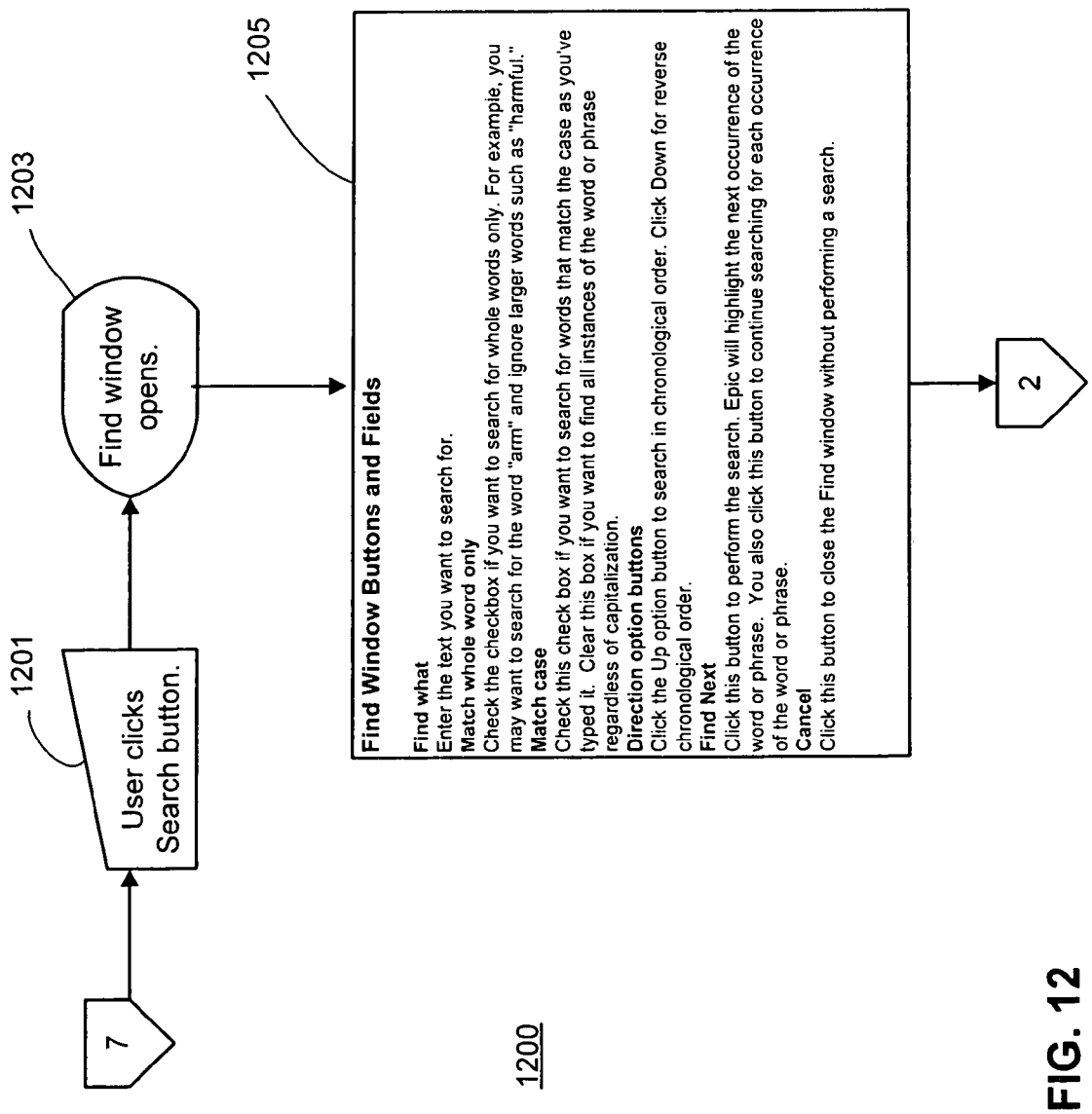
FIG. 12 is a flowchart representing a workflow for searching patient notes in accordance with an embodiment of the invention.

From the link 729 for the search function, the workflow 700 proceeds to the workflow 1200 illustrated in FIG. 12. If the user selects the search button, 1201, a find window (not depicted) is opened, 1203. Within the find window, the user may set search criteria, 1205. The search criteria may include text that is to be whole or partial word searched within the text of the notes, including matching case. The search direction can be set between chronological in ascending or descending order. Once a note meeting the criteria is found, it is highlighted in the notes listing window 32. Using a next button, the user may move to the next note meeting the search criteria. To exit the search function, the user presses a cancel button.

Figure 13:
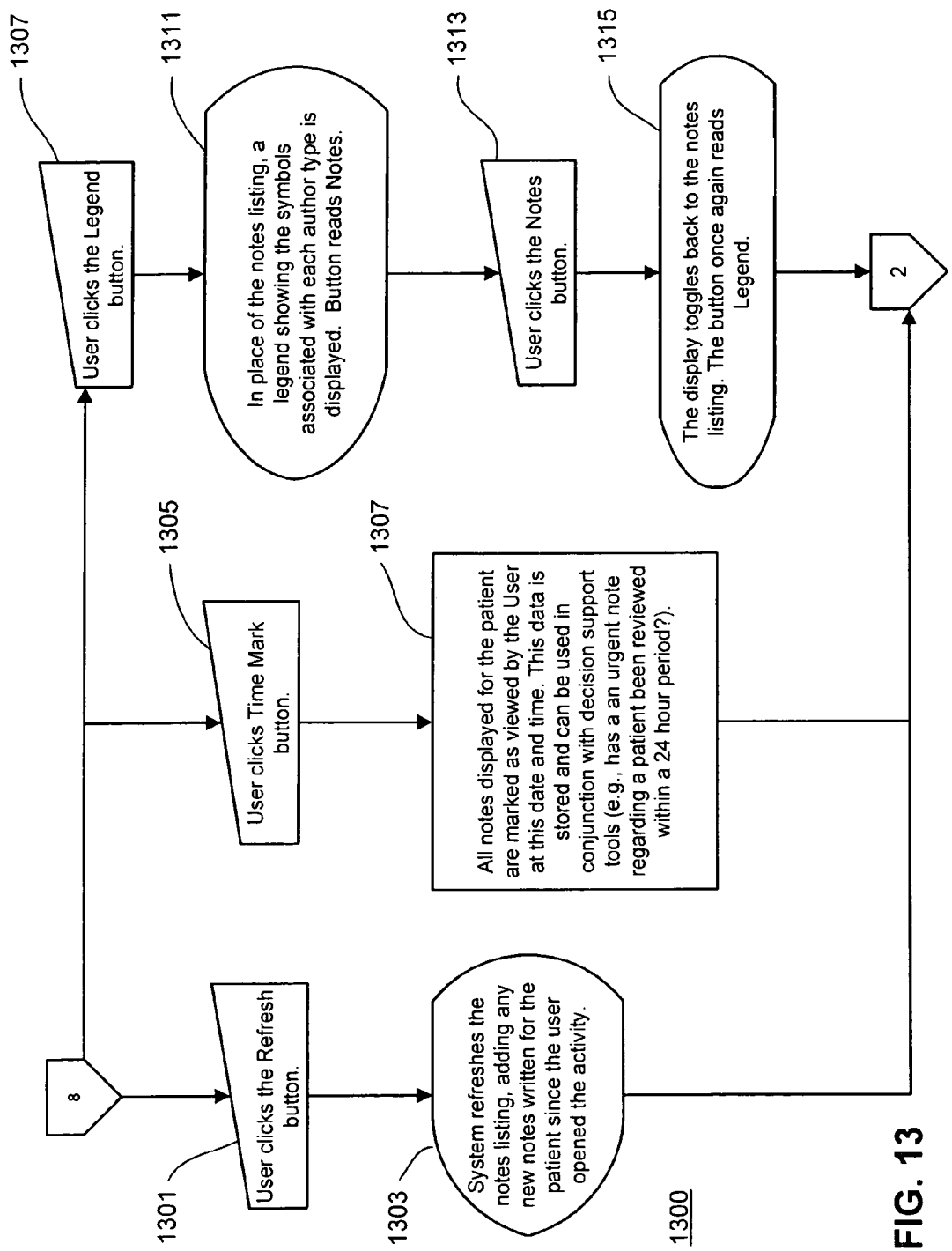
FIG. 13 is a flowchart representing a workflow for annotating a patient note in accordance with an embodiment of the invention.

From the link 731 for the legend/notes function, the workflow 700 proceeds to the workflow 1300 illustrated in FIG. 13. If the user selects the refresh button, 1301, the system 10 refreshes the listing of notes in the notes listing window 32, 1303. If the user selects the time mark button, 1305, all notes displayed for the patient are marked as viewed by the user as of that current date and time. This time mark data is stored within the system 10, and is available for use in conjunction with decision support tools (e.g., has an urgent note regarding the patient been reviewed within the last 24 hour period). If the user selects the legend button, 1309, the notes listing in the notes listing window 32 is replaced with a legend showing the symbols associated with each author type, 1311. When the user selects the notes button, 1313, the notes listing window 32 toggles back to the notes listing, 1315.

Figure 14:
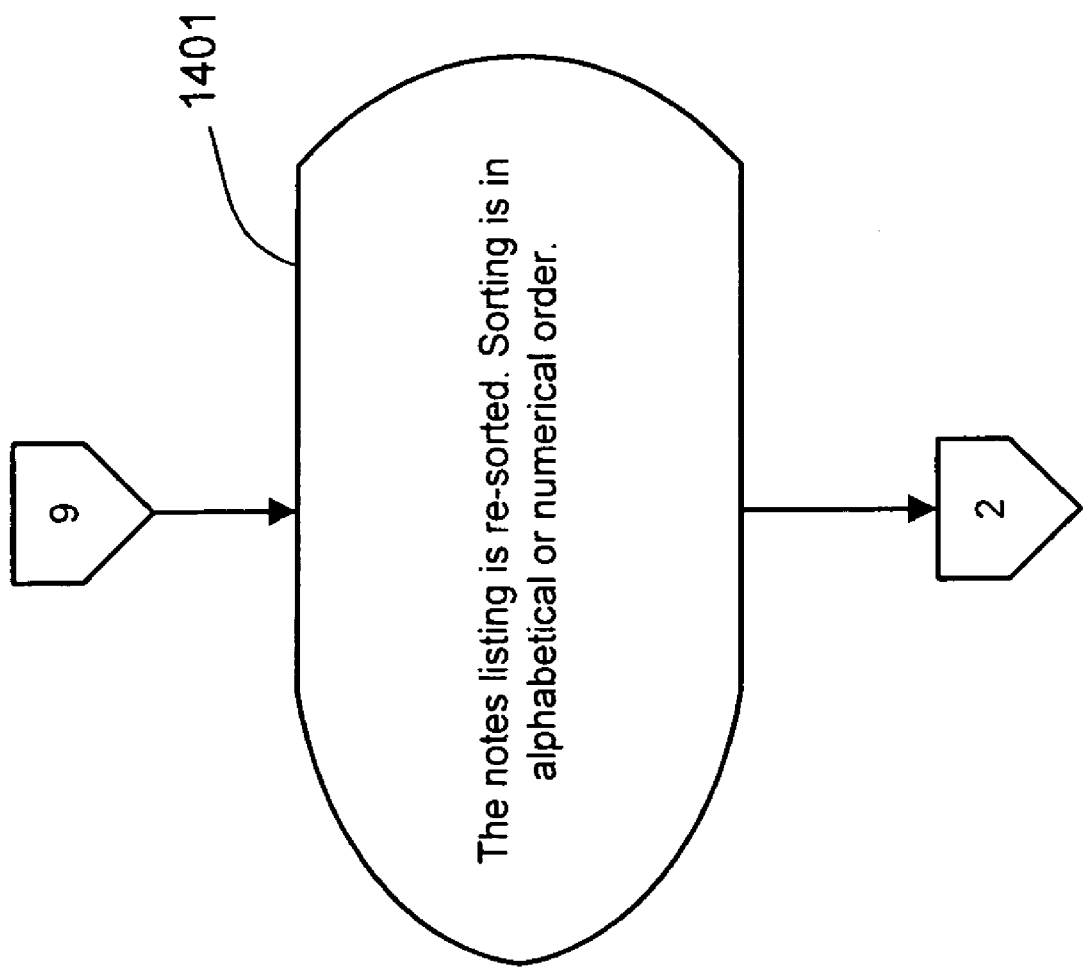
FIG. 14 is a flowchart representing a workflow for sorting patient notes in accordance with an embodiment of the invention.

From the link 735 for the notes listing column function, the workflow 700 proceeds to the workflow 1400 illustrated in FIG. 14. Upon selecting the notes listing column function, the notes listing in the notes listing window 32 is re-sorted in ascending or descending order on the basis of the information listed in the selected column, 1401. Sorting is in alphabetical or numerical order depending on the type of information in the column. The user can click the column again to reverse the sort order from ascending to descending, or vice versa.

Figure 15:
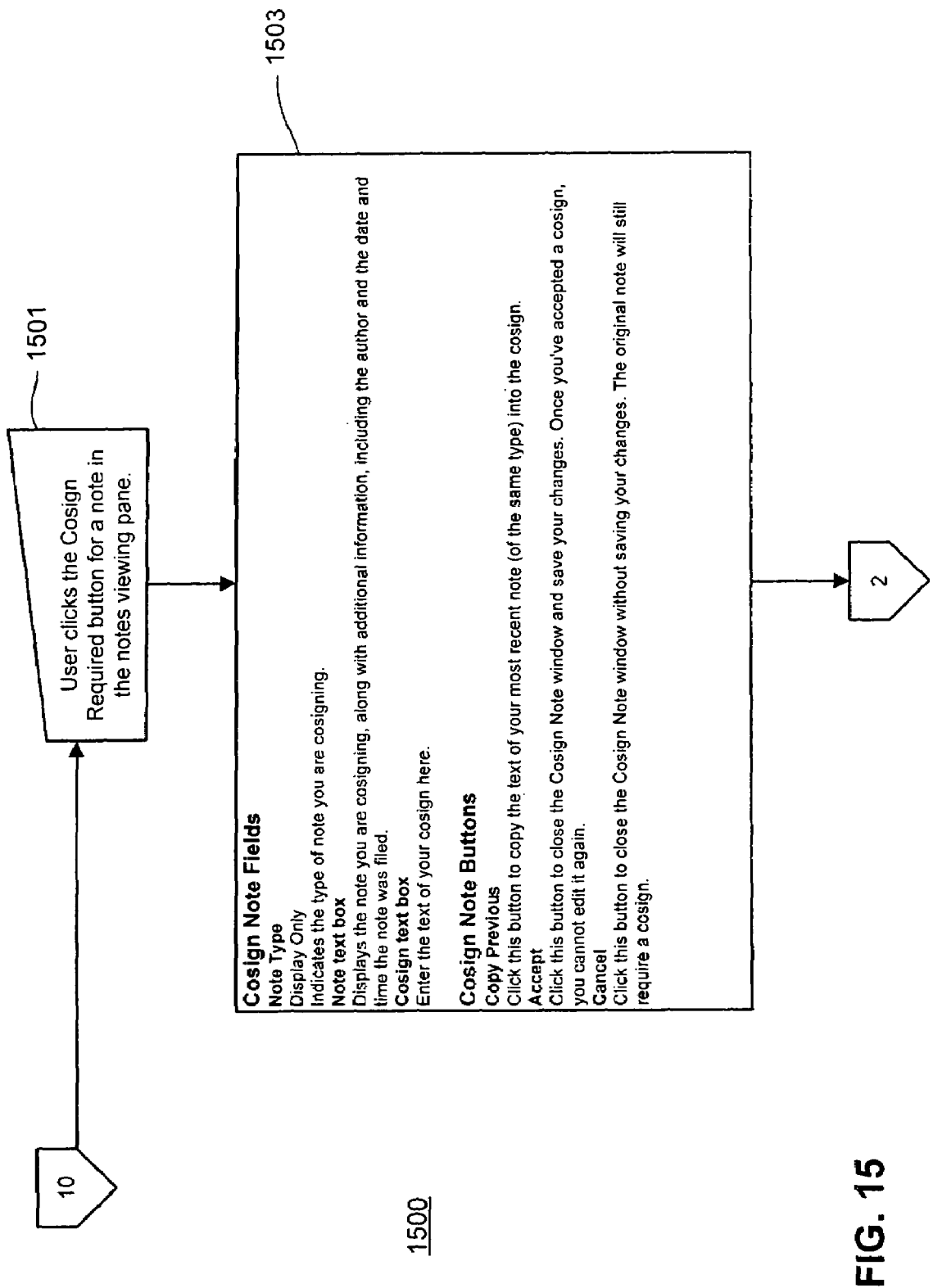
FIG. 15 is a flowchart representing a workflow for cosigning a patient note in accordance with an embodiment of the invention.

From the link 739 for the cosign function, the workflow 700 proceeds to the workflow 1500 illustrated in FIG. 15. Upon selecting the cosign required button for a note in the notes viewing pane, 1501, the cosign note window 66 is opened. Fields within the cosign note window 66 includes note type box indicating the type of note being cosigned, a note text box displaying the note text along with additional information including the author and the data and time the note was filed, and cosign text box allowing the cosigning user to enter text in connection with cosigning the note, 1503.

Figure 16:
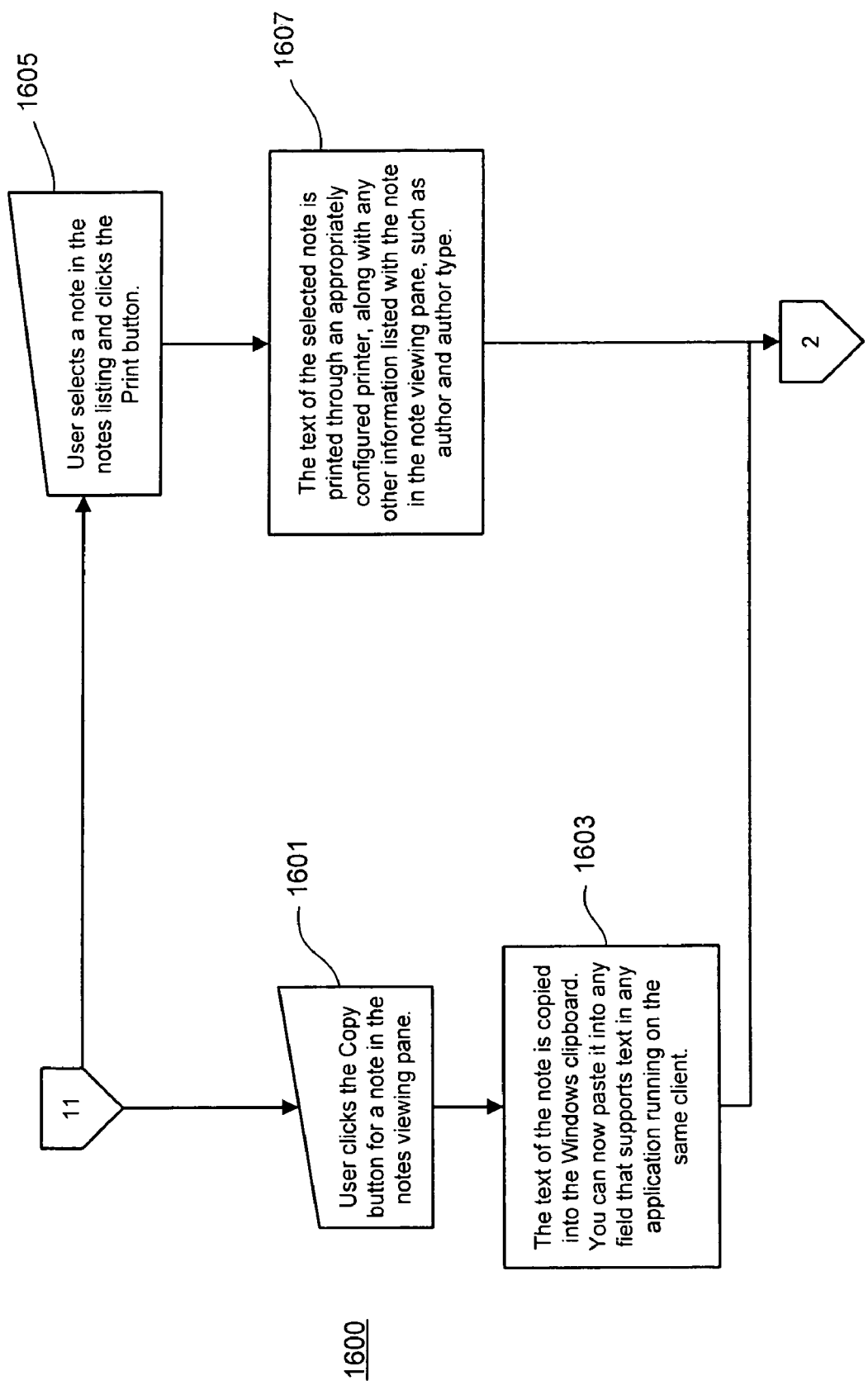
FIG. 16 is a flowchart representing a workflow for printing and/or copying a patient note in accordance with an embodiment of the invention.

From the link 733 for the print function and the link 741 for the copy function, the workflow proceeds to the workflow 1600 illustrated in FIG. 16. Upon selecting the copy button for a note from the notes viewing window 34, 1601, the text of the note is copied onto a clipboard, such as the Windows clipboard, 1603. From the clipboard the text may be copied to other notes or may be copied to other applications. Upon selecting the print button for a note from the notes viewing window 34, 1605, the text of the selected note is printed through an appropriately configured printer along with any other information listed with the note in the note viewing window 34, 1607. Types of other information include author and author type.

The invention has been described in terms of several embodiments, including a number of features and functions. Not all features and functions are required for every embodiment of the invention, and in this manner the invention provides a flexible system by which a user may document and use clinical patient information. The features discussed herein are intended to be illustrative of those features that may be implemented; however, such features should not be considered exhaustive of all possible features that may be implemented in a system configured in accordance with the embodiments of the invention.

We claim:

1. A system for documenting patient information from multiple caregivers comprising:

a health record system including a plurality of data elements, the data elements including patient note data acquired from multiple caregivers, the patient note data including at least a first patient note and a second patient note related to the care of a given patient; and a first interface and a second interface coupled to the health record system each including a graphic display, the first interface and second interface operable to retrieve, based upon information received from a first and second user, patient note data associated with a specified patient, and to graphically depict the patient note data in list form and text form within the graphic displays, each of the first and second interfaces further including an editor operable with the interface to facilitate editing of the patient notes within the graphic display;

wherein the first interface is adapted to lock the first patient note when the first user is editing the first patient note such that the second interface maintains view access to the patient notes but is denied write access to the first patient note while the first user is editing the first patient note, and wherein the second interface is adapted to simultaneously lock the second patient note when the second user is editing the second patient note such that the first interface maintains simultaneous view access to the patient notes but is denied write access to the second patient note while the second user is editing the second patient note; and wherein each interface further includes a role-based security scheme that limits at least one of the first and second user's viewing and editing access to the patient note data associated with the specified patient to only limited types of information based on a role of the user.

2. The system of claim 1, wherein the editor is operable with the interface to facilitate creation of patient note data.

3. The system of claim 1, wherein the editor is operable independent of the depiction of the patient note data within the graphic display.

4. The system of claim 1, wherein the plurality of caregivers are associated with a plurality of medical services.

5. The system of claim 1, wherein the plurality of caregivers are associated with a plurality of related medical services.

6. The system of claim 1, wherein the interface further comprises a filter for selecting particular patient note data for depiction within the graphic display.

7. The system of claim 6, further comprising filter criteria associated with the filter, the filter criteria comprising at least one of: author, author type and time.

8. The system of claim 1, wherein the patient note data is linked by time stamp data.

9. The system of claim 8, wherein the patient note data is graphically depicted within the graphic display according to the time stamp data.

10. The system of claim 1, wherein the interface further comprises a searcher operable with the interface to facilitate searching of the patient note data for depiction within the graphic display.

11. The system of claim 10, wherein the patient note data includes tag data, and wherein the searcher is operable on the tag data.

12. The system of claim 1, wherein the patient note data includes cosign data.

13. The system of claim 12, wherein the cosign data comprises a cosign from at least one caregiver.

14. The system of claim 12, wherein the cosign data comprises cosign requirement data, the cosign requirement data specifying a number of required cosigns.

15. The system of claim 1, wherein the patient note data comprise soft-deleted data.

16. A method of documenting patient note data within a health record system, the health record system including data structures for storing the patient note data, provider data and user data, the method comprising the steps of:

collecting first and second patient note data from a plurality of caregivers and storing the patient note data in at least one of the data structures;

providing a first interface and a second interface coupled to the health record system, each interface including a graphic display and an editor operable with the interface to facilitate editing of the patient note data within the graphic display, and for a patient, listing the patient note data in a first portion of each graphic display and text linked with the patient note data in a second portion of each graphic display;

locking the first patient note data when a first user of the first interface is editing the first patient note data such that a second user of the second interface maintains view access to the patient note data but is denied write access to the first patient note data while the first user is editing the first patient note data, and locking the second patient note data when the second user of the second interface is editing the second patient note data such that the first user maintains simultaneous view access to the patient note data but is denied write access to the second patient note data while the second user is editing the second patient note data; and limiting at least one of the first and second user's viewing and editing access to the patient note data associated with the specified patient only to limited types of information based on a role of the user.

17. The method of claim 16, further comprising filtering the patient note data to provide filtered patient note data and listing the filtered patient note data in the first portion of the graphic display and text linked with the filtered note data in the second portion.

18. The method of claim 16, wherein the step of collecting patient note data from a plurality of caregivers comprises collecting patient note data from a plurality of unrelated caregivers.

19. The method of claim 16, wherein the step of collecting patient note data from a plurality of caregivers comprises collecting patient note data from a plurality of related caregivers.

20. The method of claim 16, wherein the patient note data comprises time stamp data, and wherein the step of listing the patient note data comprises listing the patient note data according to the time stamp data.

21. The system of claim 16, wherein the patient note data includes tag data, and wherein the method further comprises the step of assembling a report of the patient note data based upon the tag data.

22. The system of claim 16, wherein the patient note data includes cosign data, and wherein the method further comprises the step of cosigning the patient note data in accordance with the cosign data.

23. The system of claim 16, wherein the patient note data comprises soft delete data, and wherein the method further comprises storing the patient note data in accordance with the soft delete data.

* * * * *